(12) United States Patent
McKee et al.

(10) Patent No.: US 8,544,339 B2
(45) Date of Patent: Oct. 1, 2013

(54) LIFE MONITOR FOR A WELL ACCESS LINE

(75) Inventors: L. Michael McKee, Friendswood, TX (US); Robert Michael Ramsey, Missouri City, TX (US); Hifzi Ardic, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 599 days.

(21) Appl. No.: 12/694,869

(22) Filed: Jan. 27, 2010

(65) Prior Publication Data
US 2011/0154908 A1    Jun. 30, 2011

Related U.S. Application Data

(60) Provisional application No. 61/290,908, filed on Dec. 30, 2009.

(51) Int. Cl.
*G01N 3/08* (2006.01)
(52) U.S. Cl.
USPC ............................................. 73/829
(58) Field of Classification Search
USPC ............................................. 73/829
See application file for complete search history.

(56) References Cited

U.S. PATENT DOCUMENTS

| | | | |
|---|---|---|---|
| 5,767,671 A | 6/1998 | McCoy et al. | |
| 5,963,033 A | 10/1999 | Booker | |
| 6,111,405 A | 8/2000 | Yamakawa et al. | |
| 6,321,596 B1 | 11/2001 | Newman | |
| 7,051,812 B2 | 5/2006 | McKee et al. | |
| 7,172,038 B2 * | 2/2007 | Terry et al. | 175/45 |
| 7,281,585 B2 | 10/2007 | Zheng | |
| 7,389,183 B2 * | 6/2008 | Gray | 702/6 |
| 7,444,861 B2 | 11/2008 | De Jesus et al. | |
| 7,458,267 B2 | 12/2008 | McCoy | |
| 7,637,162 B2 | 12/2009 | Nelson et al. | |
| 7,926,579 B2 * | 4/2011 | Sbordone et al. | 166/384 |

\* cited by examiner

*Primary Examiner* — Lisa Caputo
*Assistant Examiner* — Octavia Davis-Hollington
(74) *Attorney, Agent, or Firm* — Michael Flynn; Robin Nava; Timothy Curington

(57) ABSTRACT

A well access line monitor. The monitor may be employed to directly interface and establish the current yield strength of a plastically deformable line such as coiled tubing or slickline. Such interfacing may take place in advance of, or during an application. Thus, the fitness of the line for the application may be established in real-time. Further, with comparison to a reference log of projected yield strength for the line over the course of multiple bend cycles, the remaining life of the line may also be established.

12 Claims, 6 Drawing Sheets

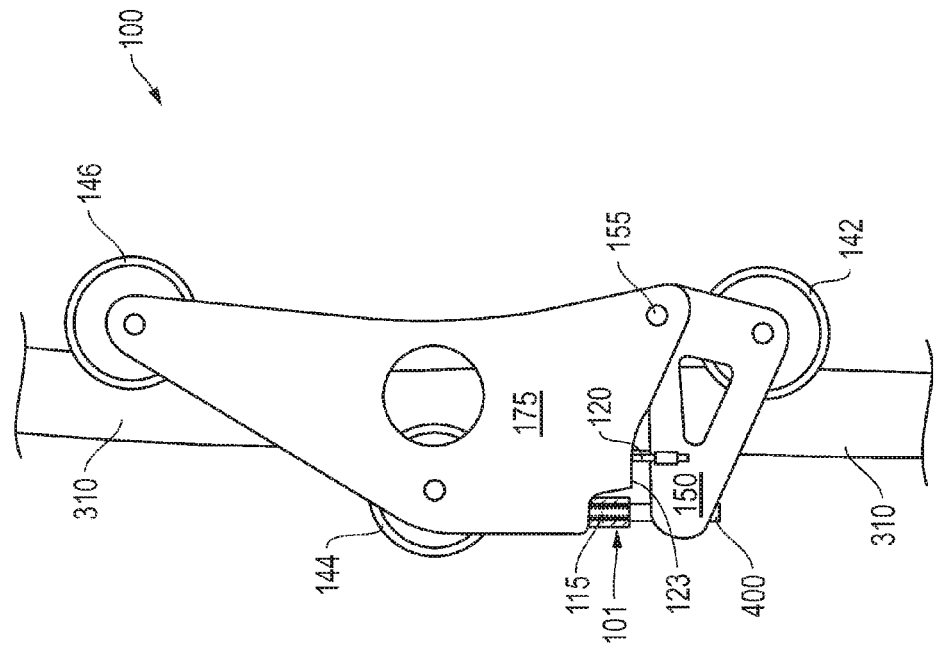
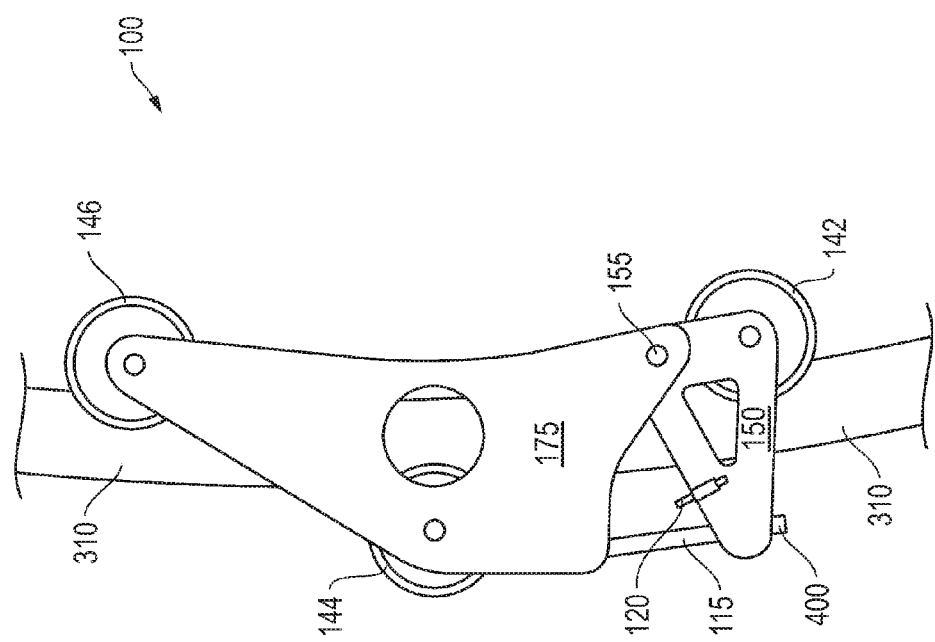

LIFE MONITOR FOR A WELL ACCESS LINE

CROSS REFERENCE TO RELATED APPLICATION

This Patent Document claims priority under 35 U.S.C. §119(e) to U.S. Provisional Application Ser. No. 61/290,908, filed on Dec. 30, 2009, which is incorporated herein by reference in its entirety.

FIELD

Embodiments described relate to devices and techniques for addressing issues related to advance warning of line failure in a well at an oilfield. That is, coiled tubing, slickline and other well access lines may be prone to cycle fatigue, cracking, or ballooning over the course of many application runs in a well. Thus, embodiments are detailed herein for the real-time monitoring of the yield strength of a well access line as it is taken from a reel for a downhole well application.

BACKGROUND

Exploring, drilling and completing hydrocarbon and other wells are generally complicated, time consuming and ultimately very expensive endeavors. As such, tremendous emphasis is often placed on well access in the hydrocarbon recovery industry. That is, access to a well at an oilfield for monitoring its condition and maintaining its proper health is of great importance. As described below, such access to the well is often provided by way of coiled tubing or slickline as well as other forms of well access lines.

Well access lines as noted may be configured to deliver interventional or monitoring tools downhole. In the case of coiled tubing and other tubular lines, fluid may also be accommodated through an interior thereof for a host of downhole applications. Coiled tubing is particularly well suited for being driven downhole, to depths of perhaps several thousand feet, by an injector at the surface of the oilfield. Thus, with these characteristics in mind, the coiled tubing will also generally be of sufficient strength and durability to withstand such applications. For example, the coiled tubing may be of stainless steel or other suitable metal based material.

In spite of being constructed of a relatively heavy metal based material, the coiled tubing is plastically deformed and wound about a drum to form a coiled tubing reel. Of course, a reel of slickline may also be provided in a similar fashion with a degree of plastifying deformation also occurring. Regardless, by making a reel of line available, these lines may be manageably delivered to the oilfield for use in a well thereat. In the case of slickline, once positioned at the oilfield, the line may be unwound from the reel and dropped vertically into the well to deliver tools coupled to the end thereof. In the case of coiled tubing, the tubing may be directed through the well by way of the noted injector equipment at the oilfield surface.

Unfortunately, due to the noted plastifying deformation which takes place during winding and unwinding of the above noted lines, yield strength is affected. That is, the amount of force necessary to achieve plastic deformation of a given line becomes less and less over time. So, for example, a coiled tubing that is rated 80,000 PSI in yield strength before initial use, may drop to a yield strength of 40,000 PSI after several dozen or so occurrences of winding and unwinding, or "cycling", for applications at well sites.

Such repeated cycling as noted above leaves the line prone to cracking. So, for example, a threshold of a 40,000 PSI rating may be set, below which, a line may no longer be used. In this manner, the possibility of cracking may be avoided. In the case of slickline, such cracking could lead to breaking of the line, stranding downhole tools in the well along with a potentially significant amount of the line itself. In the case of coiled tubing, leaking may be a more likely occurrence.

In addition to cracking, coiled tubing faces the additional risk of ballooning, wherein internal hydraulic pressure of the tubing reaches a level that certain locations of the tubing are no longer able to withstand, leading to plastic diametral growth, or "ballooning", and potentially bursting at such locations. That is, a reduction in the yield strength of the coiled tubing may be directly correlated with the likelihood of ballooning depending on the amount of differential pressure (e.g. hoop stress) that is imparted through the tubing. For example, the risk of ballooning is generally considered practical and likely when hoop stress exceeds 15% of yield strength. Thus, efforts are made to keep hoop stress below such a fairly predictable threshold as it corresponds to yield strength. This is in addition to refraining from coiled tubing use when the yield strength drops below a predetermined level (i.e. note the 40,000 PSI above).

Unfortunately, even though safe thresholds may be established for coiled tubing and slickline use, the ability to reliably stay below such thresholds is largely lacking. For example, depending on the specific make of a given line, modeling software may be used to generate a reference log which is able to predict remaining cycles to failure for the line over the course of its use. Thus, theoretically, the line may be tracked with each winding and unwinding. In turn, each subsequent user may then note the current cycle and reference the log to make sure that no thresholds are exceeded in relation to an application to be run. However, the use of such a reference log requires proper tracking of prior line deployments. That is, such tracking introduces the possibility of human error. Even simple mislabeling or incorrect entry of a serial number into the tracking system may render this technique unreliable.

Even where no human error is present for the technique described above, neither is any direct measurement. At best, this technique of predicting cycle life provides a user with a guess of what actual remaining life may be. Of course, this depends on the accuracy of the modeling software or the actual specifications of the line, which generally vary from the assumed specifications to a degree. Furthermore, even in the case of coiled tubing, where direct real-time measurement may be acquired by an integrity monitor which interfaces the line to check for ballooning, no yield strength data is provided. Thus, the possibility of cracking or emerging ballooning remains undetected. Ultimately, in order to avoid the exorbitant costs associated with line replacement at the well site, down time, and any necessary clean-up following line failure, the substantial costs of prematurely discarding coiled tubing and/or slickline are willingly incurred.

SUMMARY

A device is disclosed for monitoring a condition of a well access line such as coiled tubing or slickline. The device is employed during plastic deformation, such as straightening of the line, for a well application and includes a frame which accommodates a bending mechanism and a strain gauge. The strain gauge is coupled to the bending mechanism to obtain load information therefrom during the straightening or bending process.

In one embodiment, the device or straightening mechanism may include first and second rollers for positioning against a first side of the line, whereas a third roller is configured for positioning against a second side of the line opposite the first side and between the other rollers. A frame which accommodates all of the rollers also accommodates a strain gauge coupled to one of the rollers that is of adjustable positioning for straightening of the line.

A method of monitoring a well access line is also provided. The method includes establishing a yield strength reference log for the line and physically interfacing the line to determine a current yield strength. Thus, the current yield strength may be compared with the yield strength reference log to establish one of an estimated remaining cycle life of the line and an estimated ballooning pressure tolerance thereof.

BRIEF DESCRIPTION OF THE DRAWINGS

FIG. 4A is a side view of the life monitor of FIG. 1 accommodating the coiled tubing of FIG. 3.

FIG. 4B is a side view of the life monitor of FIG. 1 monitoring a condition of the coiled tubing of FIG. 3 through straightening thereof.

DETAILED DESCRIPTION

Embodiments of a life monitor for a well access line are described with reference to certain coiled tubing applications. As such, certain configurations of a life monitor for accommodating coiled tubing are depicted. For example, a life monitor is depicted incorporated into an injector assembly, which in turn is utilized to advance coiled tubing to a cleanout site in a well. However, a variety of other well access lines and applications may take advantage of embodiments of life monitors as detailed herein. For example, slickline and any other access line which is routinely plastically deformed about a reel for transport may be particularly well suited for evaluation and/or monitoring by a life monitor as described herein. Embodiments of a life monitor take advantage of a bending mechanism of the monitor which is applied to the line being monitored. As used herein, the term "bending" is employed in a relative sense. So, for example, even where a wound coiled tubing is unwound or undergoes a reverse bend which may include complete straightening thereof, this may still be referenced as 'bending'. Thus, the mechanism described may be referenced as a bending mechanism for bending of the coiled tubing even where employed for bending to achieve 'straightening'. Regardless, a strain gauge may be coupled to the bending mechanism to obtain load information therefrom. Such information may be utilized to establish real-time yield strength of the line.

Figure 1:
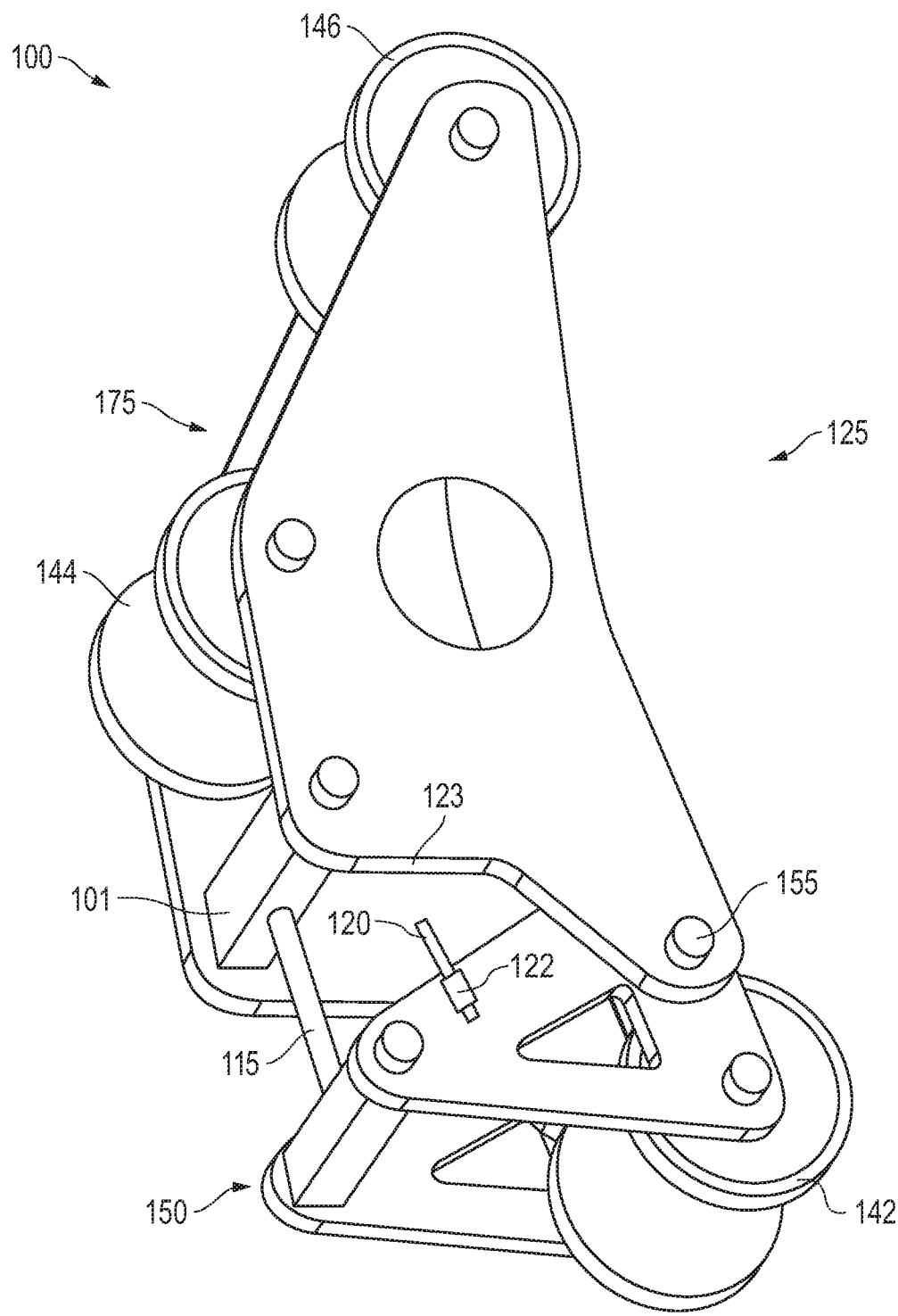
FIG. 1 is a front perspective view of an embodiment of a life monitor for a well access line.

Referring now to FIG. 1, an embodiment of a life monitor 100 is depicted. In this embodiment, a frame 125 is provided which accommodates three rollers 142, 144, 146. With added reference to FIGS. 4A and 4B, the intermediate roller 144 is configured to be disposed at one side of a well access line such as coiled tubing 310. Alternatively, opposite rollers 142, 146 are configured to be disposed at an opposite side of such a line. In the embodiment shown, the intermediate roller 144 may be configured to aid in driving of a line through the monitor 100, particularly in a handheld embodiment as detailed further herein. However, the other rollers 142, 146 are considered idle. Furthermore, in other embodiments, any combination of the rollers 142, 144, 146, may be employed in driving of a line such as coiled tubing 310 therethrough. Indeed, in one embodiment an injector assembly 200 advances a line through the monitor 100 without the aid of any of the rollers 142, 144, 146 (see FIG. 2).

Continuing with reference to FIG. 1, with added reference to FIGS. 4A and 4B, at least one of the rollers 142, 144, 146 is configured to be movable relative the other two. In this manner, a line such as coiled tubing 310 may be straightened as it is passed between the rollers 142, 146 at one side of the frame 125, and the intermediate roller 144 at the other side of the frame. In the embodiments detailed herein, such movability is provided to one of the non-intermediate or 'opposite' rollers 142 relative to the other two 144, 146. However, in an alternate embodiment, the other opposite roller 146 or even the intermediate roller 144 may be configured to be movable for straightening of a well access line such as coiled tubing 310.

In the embodiment shown, the noted 'movability' is provided by the frame 125, which is made up of adjacent sections 150, 175. Indeed, it is these sections 150, 175 which are movable relative to one another (i.e. about a pivot 155). Thus, the particular roller 142 which is accommodated by this section 150 is movable relative to the other two rollers 144, 146. Again, this is particularly visible with reference to FIGS. 4A and 4B in which angular movement of a section 150 about the pivot 155 translates into straightening of the noted coiled tubing 310 which is accommodated between the rollers 142, 144, 146. For sake of clarification, the section 150 which accommodates the movable roller 142 relative the other two is referenced herein-below as the movable section 150 whereas the other section is referenced as the stationary section 175. However, in a relative sense either section 150, 175 may be considered as movable with respect to the other.

Continuing again with reference to FIGS. 1, 4A and 4B, in conjunction with the above noted straightening, the monitor may be employed to detect a yield strength of the coiled tubing 310. So, for example, where the movable section 150 is configured to move toward the stationary section 175 in order to straighten the coiled tubing 310, a particular amount of force will be required. In the case of typical carbon-steel coiled tubing 310, this force may be in a range of between about 40,000 PSI and about 120,000 PSI and is referred to herein as the yield strength of the tubing 310. As noted above, the yield strength of the coiled tubing 310 may vary over time as the tubing 310 is repeatedly plastically deformed as it is unraveled and re-wound over the course of various deployments. Thus, as described below, this yield strength may be monitored in conjunction with the typical straightening of a line that accommodates line deployment and retrieval applications.

With particular reference to FIG. 1, the yield strength at any given point in time of straightening may be detected by a conventional load cell 101. That is, in the embodiment shown, a load cell 101 is provided which is coupled to the movable section 150 via an adjustment screw 115. That is, as the screw 115 is tightened, the movable section 150 is brought into closer proximity to the load cell 101 and the stationary section 175. However, with added reference to FIGS. 4A and 4B, the coiled tubing 310 is also straightened as the movable section 150 is brought toward the stationary section 175 and the tubing advanced through the monitor 100. Thus, tension, which is indicative of the above-noted yield strength, is translated through the screw 115 and to the load cell 101.

Of course, the degree of accuracy in determining yield strength via tension through the screw 115, is dependent upon the degree of accuracy in the straightening of the coiled tubing 310 or other line. Thus, in order to ensure that the coiled tubing 310 is properly straightened, an adjustable straightening stop 120 is provided at the movable section 150. The stop 120 is configured for contacting a face 123 of the stationary section 175. As such, the stop 120 regulates how close the movable section 150 may be brought toward the stationary section 175 via tightening of the screw 115. The positional setting of the stop 120 is dependent upon the dimensions of the coiled tubing 310 or other line to be straightened.

Figure 2:
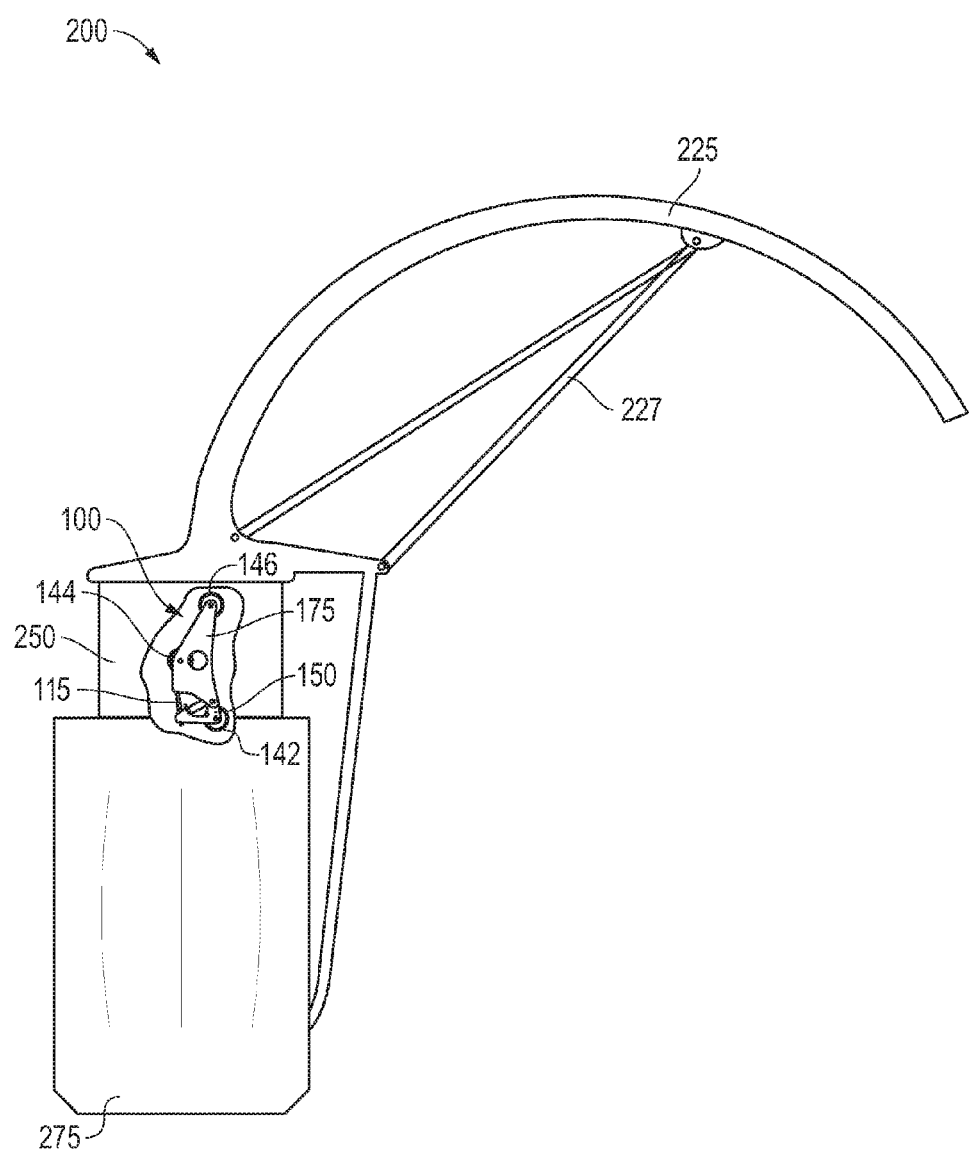
FIG. 2 is a partially sectional side view of an injector assembly housing the life monitor of FIG. 1.
Figure 3:
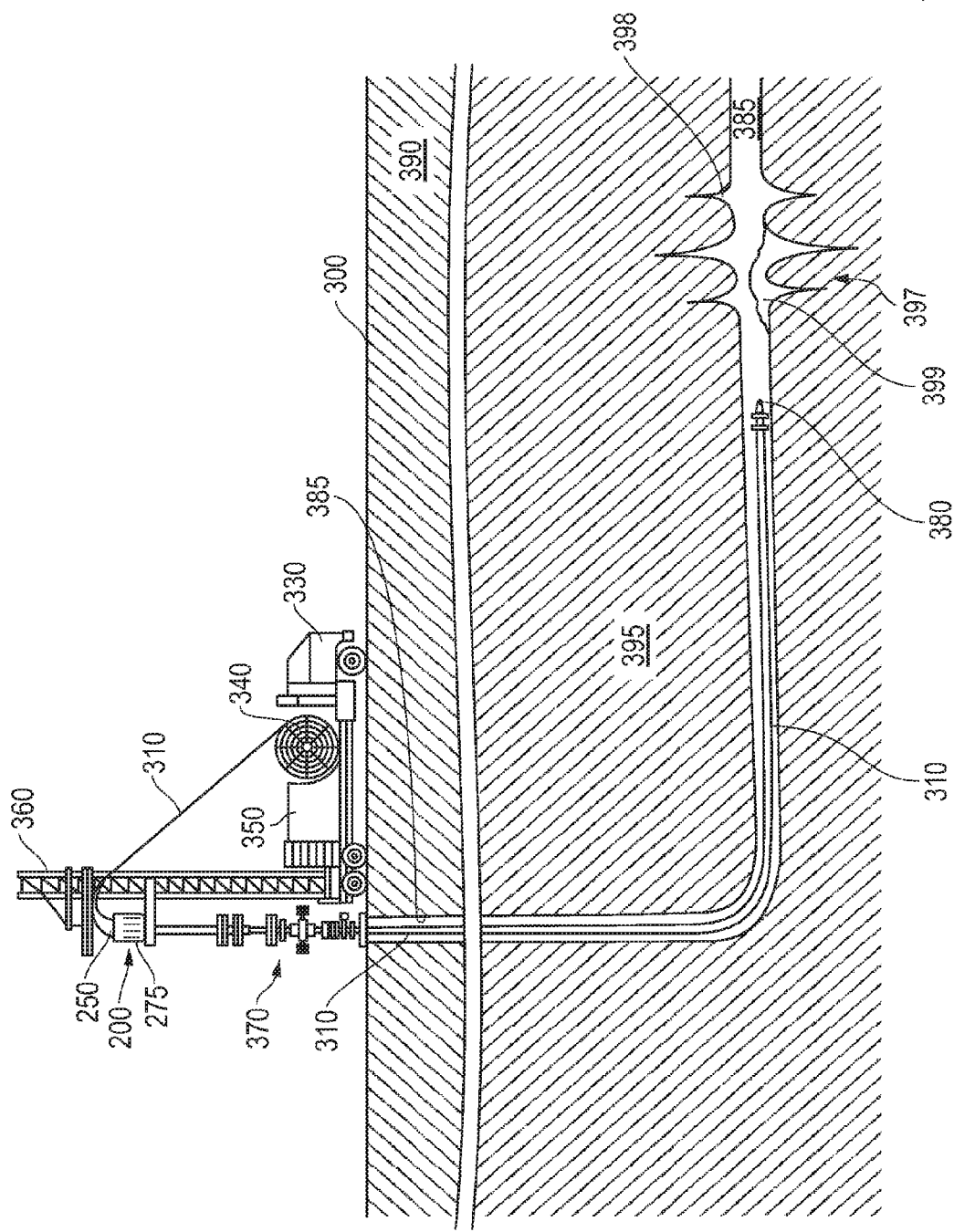
FIG. 3 is an overview of an oilfield accommodating the injector assembly of FIG. 2 for advancement of an access line in the form of coiled tubing through a well.

Referring now to FIG. 2, with added reference to FIG. 3, a partially sectional view of an injector assembly 200 is depicted. The assembly 200 incorporates the life monitor 100 of FIG. 1 at a housing 250 positioned over a conventional injector 275. The assembly 200 includes a gooseneck guide 225 for directing unwinding coiled tubing 310 from a reel 340. Once in the housing 250, the coiled tubing 310 may be straightened by the monitor 100 on its way to the injector 275 for driving into a well 385 as depicted in FIG. 3. Indeed, the monitor 100 is aligned to receive the coiled tubing 310 from the gooseneck guide 225 between the intermediate 144 and opposite 142, 146 rollers. Thus, as detailed above, subsequent movement of the movable section 150 relative the stationary section 175 via the adjustment screw 115 may be employed to both continuously straighten the coiled tubing 310 and determine its yield strength.

Continuing with reference to FIGS. 2 and 3, the straightening of the unwinding coiled tubing 310 is achieved via a reverse bend that is induced by the monitor 100 as described above. More specifically, a roller 142 at the movable section 150 of the monitor 100 is moved so as to physically interface and continuously reverse bend (i.e. straighten) the advancing coiled tubing 310. However, in alternate embodiments such a reverse bend may be induced by different means. For example, in one embodiment a hydraulic cylinder or arm may be coupled to the intermediate roller 144 so as to adjust its position relative the other rollers 142, 146. As such, a reverse bend or straightening of advancing coiled tubing 310 may be achieved. In such an embodiment, forces on the cylinder which are necessary to hold the intermediate roller 144 in place and achieve the noted straightening may be monitored. For example, a conventional pressure transducer may be coupled to the cylinder. Regardless, such monitoring may again be utilized to track the yield strength of the coiled tubing in real-time.

Referring now to FIG. 3, an overview of an oilfield 300 is shown at which the injector assembly 200 of FIG. 2 is accommodated. The assembly 200 is supported by a mobile rig 360 and draws the coiled tubing 310 from a reel 340 of a mobile coiled tubing truck 330. The truck 330 is equipped with a control unit 350 for directing coiled tubing operations such as a clean out application as described below. Additionally, the control unit 350 may be configured to communicate data to or from application equipment, including the monitor 100 of FIGS. 1 and 2. So, for example, data relating to the yield strength of the coiled tubing 310 may be obtained in real-time as the tubing 310 is advanced for the depicted application. Due to the proximity of the monitor housing 250, such data may be communicated wirelessly.

Continuing with reference to FIG. 3, the injector 275 of the assembly 200 may be employed to advance the coiled tubing 310 through valving and pressure control equipment 370 often referred to as a "Christmas tree". From there, the coiled tubing 310 may enter a well 385, traversing various formation layers 390, 395 and be directed to an application site such as the depicted production region 397. In the embodiment shown, the well 385 is highly deviated and perforations 398 of the production region 397 occluded with debris 399. Thus, coiled tubing 310, which is particularly well suited for use in such wells is employed, along with a clean-out tool 380. However, as described below, real-time monitoring of the yield strength of the coiled tubing 310 may also be employed so as to ensure that the coiled tubing 310 is structurally fit for the application. That is, as detailed further below, such real-time monitoring of yield strength may be employed to avoid cracking of the tubing 310 during unwinding, or ballooning from internal pressures during clean-out.

Figure 5A:
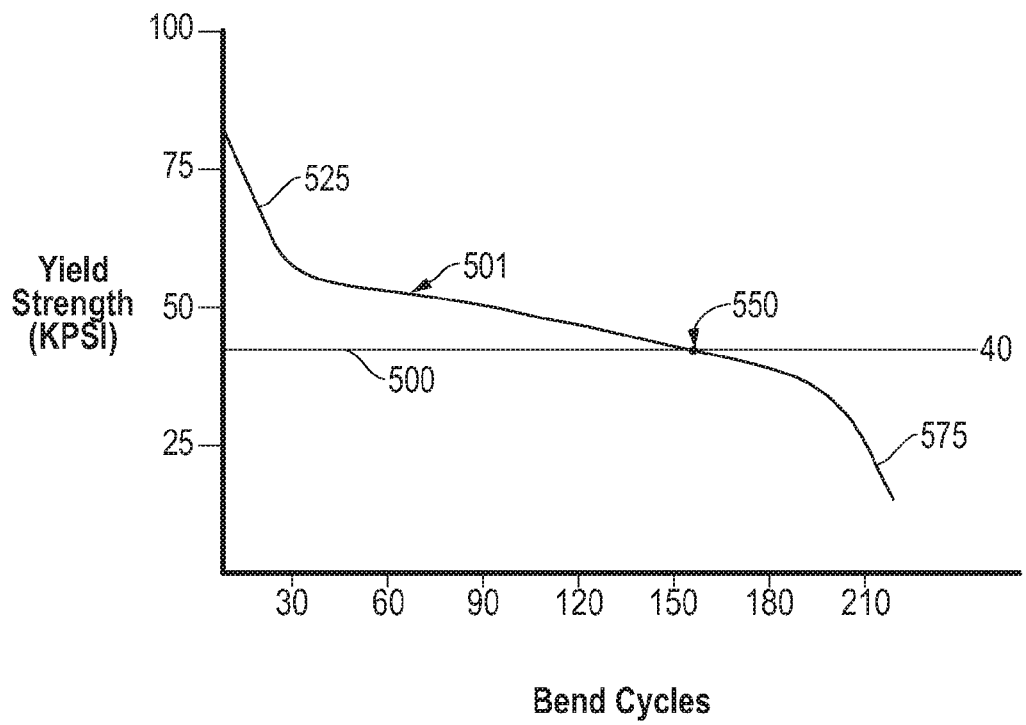
FIG. 5A is a chart for evaluating a monitored yield strength condition of the coiled tubing of FIG. 4B by the monitor of FIG. 4B.

With added reference to FIG. 5A, a yield strength reference log may be established for coiled tubing 310 or any other plastically deformable line such as slickline. This log of changing yield over the course of multiple bend cycles may be established for any given line based on historical testing and specifications (e.g. materials, dimensions, etc.). In the chart of FIG. 5A, for example, an 80,000 PSI yield strength rated coiled tubing 310 is provided that drops to a yield strength of less than about 25,000 PSI over the course of about 210 bend cycles which is roughly 70 trips in the well 385. That is, the three-fold winding and unwinding of the tubing 310 relative to the bending components of a reel 340, injector 200, and monitor 100, takes a toll on yield strength which may be predictably plotted.

Continuing with reference to FIGS. 3 and 5, it is determined that for the example embodiment of coiled tubing 310 a yield strength of more than about 40,000 PSI is necessary to prevent cracking of the tubing 310 during an application. Thus, a 40,000 PSI threshold 500 is depicted in the chart of FIG. 5A as detailed further below. With reference to FIG. 3, real-time monitoring of the yield strength of the tubing 310 may take place as described above so as to ensure that such a threshold is not crossed. Furthermore, with reference to the log of FIG. 5A, the remaining life or number of bend cycles left for the tubing 310 may also be estimated.

While avoidance of cracking may be visibly understood with added reference to FIG. 5A, the more dynamic circumstance of ballooning due to reduction in yield strength may be better understood with reference to an equation. Namely, the ballooning threshold is generally considered reached when hoop stress exceeds 15% of the yield strength. That is, there is no guarantee that ballooning will occur when such a percentage is reached. However, depending on the type of line employed, such a threshold is commonly set.

Regardless, hoop stress is a function of the differential pressure through the tubing 310, for example, during a clean-out application. More specifically, hoop stress may be estimated as this differential pressure (DP) multiplied by the inner diameter (ID) of the tubing 310 divided by 2 times its wall thickness (WT) (i.e. DP×ID/2WT). So, for example, where the DP for the clean out is 2,000 PSI run through a 2.0 inch ID coiled tubing 310 with a wall thickness of $^{3}\!/_{16}{}^{th}$ of an inch, the hoop stress on the tubing 310 is about 10,700 PSI. Thus, the noted ballooning threshold may be crossed where the monitored yield strength drops to a level that is below 71,000 PSI.

Figure 5B:
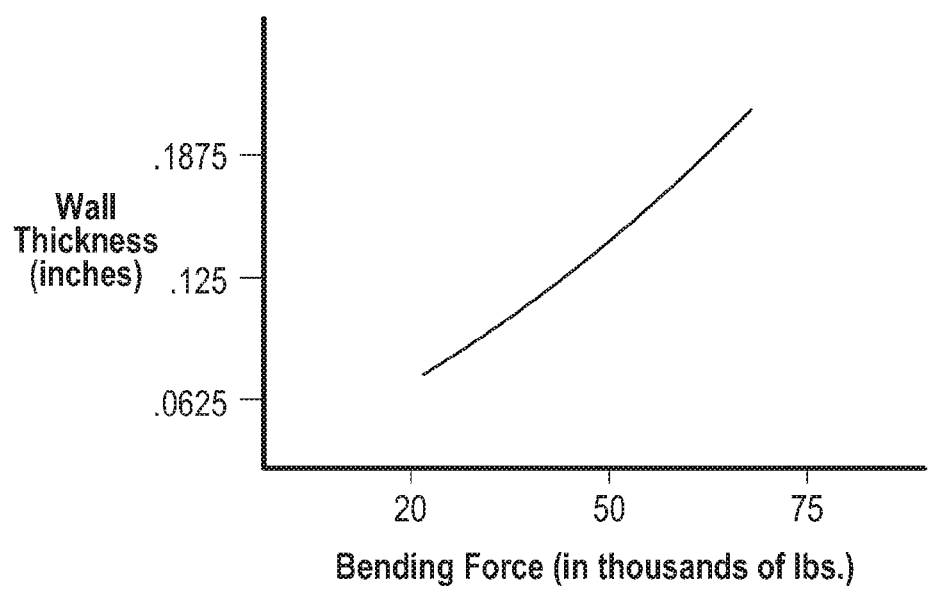
FIG. 5B is a chart comparing changes in coiled tubing wall thicknesses with forces required to achieve bending of the tubing.

With the above equation in mind and added reference to FIG. 5B, it is worth noting that the force required to deform tubing, may also be affected by acids, abrasives and other materials which are delivered through the coiled tubing 310. That is, in addition to changes in yield strength from repeated bend cycles, the tubing 310 is also prone to structural changes such as eroding or thinning of its walls. Thus, where harsh acids or abrasives are repeatedly directed through tubing 310, its thinning walls will lead to a reduction in cross sectional area which is proportional to the force required to bend tubing.

A monitor such as that described herein may be used to track required bending forces relative to the coiled tubing both before and after pumping acids, abrasives or the like. Thus, with reference to the log of FIG. 5B, the amount of thinning which has occurred over the life of the tubing may be reliably estimated. Returning briefly to FIG. 5A, it is apparent that the decline in yield strength is generally somewhat gradual after the first several bending cycles. By contrast, the thinning that is revealed with reference to FIG. 5B is a function of the substances pumped through the tubing. As such, the degree of thinning may be more rapid than what might be accounted for by a reference log such as that of FIG. 5A. Nevertheless, use of a monitor 100, assembly 200, and control unit 350 as detailed herein-above with respect to FIGS. 1-3 may help to track and prevent such circumstances of cracking or ballooning.

Referring now to FIGS. 4A and 4B, the life monitor 100 of FIG. 1 is shown straightening a portion of coiled tubing 310 as described above. More specifically, plastically bent coiled tubing 310, such as that unwound from a reel 340 of FIG. 3, is shown in FIG. 4A as initially accommodated by the monitor 100. A movable section 150 of the monitor 100 is then rotated about a pivot 155 toward a stationary section 175 thereof as shown in FIG. 4B. The degree of this rotation is predetermined based on dimensions of the coiled tubing 310. Further, the rotation itself is effectuated by the tightening of a head 400 of adjustment screw 115 which is coupled to both sections 150, 175. Indeed, the sectional cut-away of FIG. 4B reveals the screw 115 threaded through the body of a conventional load cell 101. Thus, the amount of force employed in straightening the coiled tubing 310 by the monitor 100 may be calculated.

Straightening of the coiled tubing 310 in the manner depicted in FIG. 4B may be substantially continuous. That is, as described with reference to FIG. 3, the coiled tubing 310 may be advanced through the monitor 100 throughout the course of a given downhole application. However, in alternate embodiments, the monitor 100 may be a handheld device that is not necessarily incorporated into larger surface equipment. In such embodiments, a user may employ the monitor 100 for spot checking the yield strength of the coiled tubing 310. So, for example, a user may directly employ the monitor 100 to straighten an end of the coiled tubing 310 and acquire a hands on initial check of yield strength thereat. This may even be done before threading of the coiled tubing through an injector assembly 200 for an application as depicted in FIG. 3. Thus, considerable time and expense may be saved where such an initial check reveals the coiled tubing 310 to be unsuitable for use due to current yield strength.

Referring now to FIG. 5A, a chart is shown in the form of a projected log of yield strength in thousands of PSI over the course of many bend cycles. Thus, while continuous or spot checking yield strength may tell the user whether or not a line is fit for use for a given application, it may also be used to project the remaining useful life of the line. For example, as shown in FIG. 5A, a threshold 500 of 40 KPSI is set to avoid cracking for a hypothetical coiled tubing application. Thus, when a yield strength below this is detected by the monitor 100 of FIGS. 1 and 4, the application may be pre-empted or halted. However, even where yield strength is detected that is within a safe region 501, with reference to the chart, the detection may be used to forecast the remaining life of the line (e.g. the number of bend cycles remaining before reaching the threshold 500).

With added reference to FIGS. 1 and 4, it is worth re-stating that the chart of FIG. 5A depicts a projected log of yield strength as opposed to recorded data acquired by the monitor 100. That said, the threshold 500 for the particular hypothetical application depicted may be expected to be reached at between about 50-60 trips in the well. That is, as alluded to above, each trip in the well may result in about 3 bend cycles, and, in this case a threshold reached at between about 150 and 180 bend cycles (see point 550). Thus, detections by the monitor 100 which are below this threshold 500 point to a risk of ballooning or cracking that is deemed unacceptable (see 575). However, detections by the monitor 100 which correspond to the projected safe region 501 of yield strength may proceed without undue concern.

Of additional note, the projected yield strength of the line appears to decrease at the most rapidly in first several line deployments (i.e. in the initial bend cycles 525). Depending on the particular materials and dimensions of the line, this is generally to be expected (as is usually the case in the last several bend cycles as well). By contrast, however, a more gradual decrease in yield strength is generally expected over the middle period of bend cycles. Indeed, along these lines, the entire projected log is built based on known materials, dimensions, historical testing, and other factors relevant to the particular line that is employed.

Figure 6:
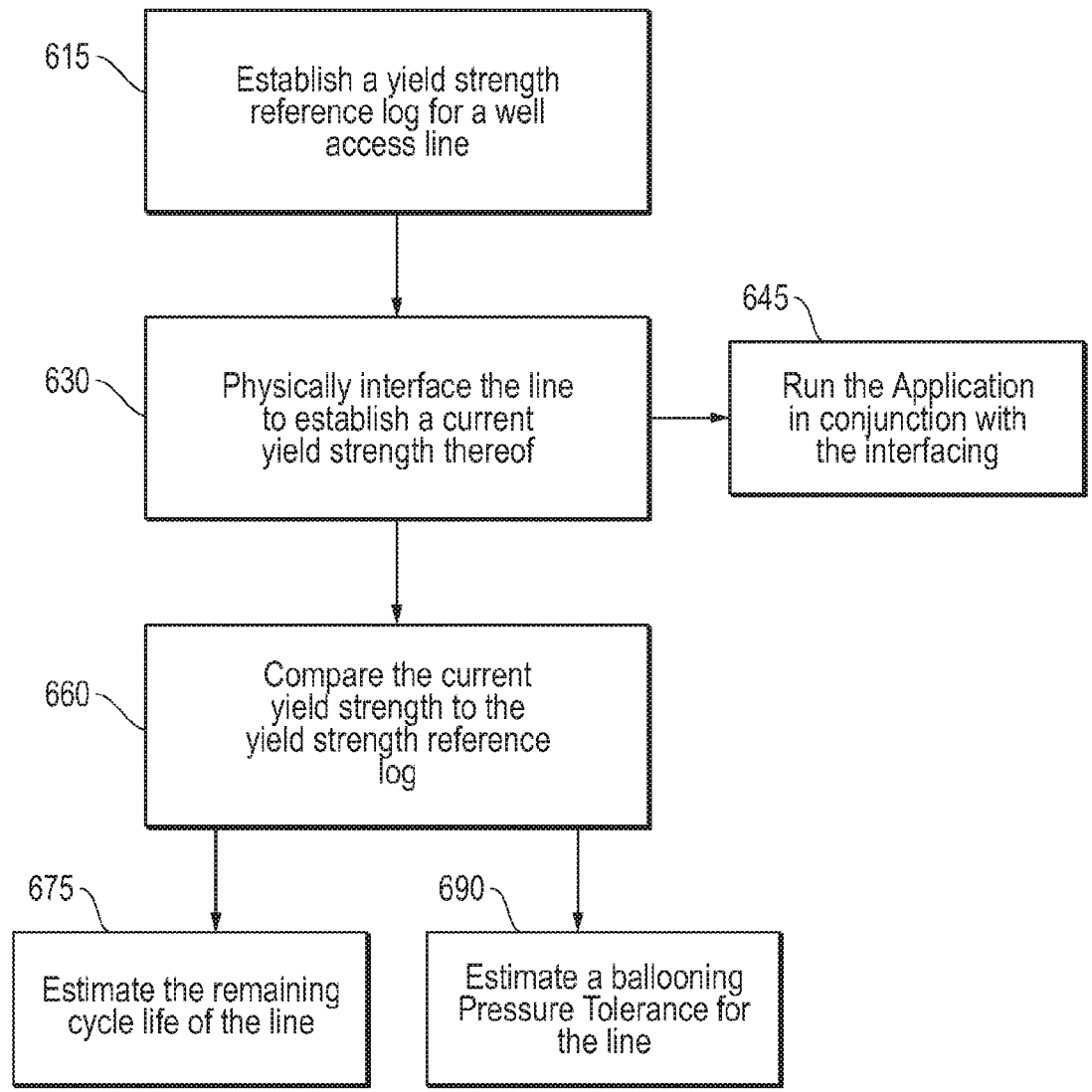
FIG. 6 is a flow-chart summarizing an embodiment of employing a life monitor for a well access line.

Referring now to FIG. 6, a flow-chart is depicted which summarizes an embodiment of employing a life monitor for a well access line. The monitor may be employed to provide a current yield strength of the line as indicated at 630. Thus, even during an application, yield strength of the line may be continuously monitored (see 645). Further, knowledge of the current yield strength may be compared against a known cracking threshold to ensure that the application is run without significant risk of cracking on the line. In fact, a yield strength reference log may even be established in advance as indicated at 615. Thus, where the current yield strength detected is compared against the reference log as indicated at 660, the remaining life of the line may be estimated (see 675).

The above noted remaining life, in terms of bend cycles, may be determined based on the reference log in light of a predetermined yield strength threshold for cracking as described above. However, as indicated at 690, in the case of tubular lines such as coiled tubing, ballooning pressure tolerance may also be estimated. In this case, known application pressure parameters may be accounted for as the current yield strength is compared against the reference log.

Embodiments described hereinabove provide a monitor and techniques for directly establishing yield strength of a well access line, for example, as an application is run with the line. Thus, real-time yield strength information may be available for the application. Further, the direct measurements provided allow for more accurate yield strength determinations. As a result, accuracy in determining the overall remaining life of the line from the time of measurement may also be improved. Thus, the odds of prematurely discarding a tremendously expensive line are dramatically reduced. Direct measurement and resultant automatic storage of yield strength data also minimizes the possibilities of human error.

The preceding description has been presented with reference to presently preferred embodiments. Persons skilled in the art and technology to which these embodiments pertain will appreciate that alterations and changes in the described structures and methods of operation may be practiced without meaningfully departing from the principle, and scope of these embodiments. Furthermore, the foregoing description should not be read as pertaining only to the precise structures described and shown in the accompanying drawings, but rather should be read as consistent with and as support for the following claims, which are to have their fullest and fairest scope.

We claim:

1. A method of monitoring a life of a well access line, the method comprising:
    establishing a yield strength reference log relative to the line;
    physically interfacing the line to determine a current yield strength thereof, the yield strength determined by measuring a force during the physical interface with the line; and
    comparing the current yield strength with the yield strength reference log to establish one of an estimated remaining cycle life of the line and an estimated ballooning pressure tolerance of the line.

2. The method of claim 1 wherein the well access line is one of a substantially solid delivery line and a tubular delivery line.

3. The method of claim 2 wherein the solid delivery line is slickline and the tubular delivery line is coiled tubing.

4. The method of claim 2 further comprising running an application in a well with the line during said interfacing and said comparing.

5. The method of claim 4 wherein the estimated remaining cycle life is based on a predetermined yield strength threshold to avoid line cracking.

6. The method of claim 5 further comprising halting the application when said comparing reveals the current yield strength less than about the yield strength threshold.

7. The method of claim 4 wherein the line is the tubular delivery line and the estimated ballooning pressure tolerance is based on hoop stress from a differential pressure through the line during the application in light of the current yield strength.

8. The method of claim 7 further comprising employing a control unit to direct the application at known differential pressure and to dynamically determine the ballooning pressure tolerance during the application based on obtained current yield strength data.

9. The method of claim 8 further comprising halting the application when the ballooning pressure tolerance of hoop stress exceeds 15% of the current yield strength as determined by the control unit.

10. A method of monitoring a yield strength of a well access line, the method comprising physically interfacing the line with a bending mechanism for determining the yield strength thereof, wherein the yield strength is determined by an amount of force measured when the bending mechanism physically interfaces with the line.

11. The method of claim 10 further comprising running an application in a well with the line, the determining continuing in real-time during said running.

12. The method of claim 11 further comprising:
    establishing a reference log to estimate yield strength of the line over numerous bend cycles based on specifications of the line; and
    comparing the determined yield strength with the reference log to establish an estimated remaining cycle life of the line.

* * * * *